United States Patent [19]

Szczepanski et al.

[11] Patent Number: 5,166,430

[45] Date of Patent: Nov. 24, 1992

[54] PROCESS FOR THE PREPARATION OF 2-(2-HALOGENOETHYLTHIO)-PHENYL-SULFONAMIDES

[75] Inventors: Henry Szczepanski, Wallbach; Willy Meyer, Riehen; Franz Weibel, Gipf-Oberfrick, all of Switzerland

[73] Assignee: Ciba-Geigy Corporation, Ardsley, N.Y.

[21] Appl. No.: 585,743

[22] Filed: Sep. 20, 1990

[30] Foreign Application Priority Data

Sep. 29, 1989 [CH] Switzerland ............... 3554/89
Aug. 15, 1990 [CH] Switzerland ............... 2654/90
Aug. 28, 1990 [CH] Switzerland ............... 2786/90

[51] Int. Cl.$^5$ ................ C07C 311/39; C07C 311/16
[52] U.S. Cl. .................................. 564/85; 564/83; 564/90
[58] Field of Search ............ 564/83, 85, 90; 568/23, 568/27, 56, 58, 67

[56] References Cited

U.S. PATENT DOCUMENTS

| | | | |
|---|---|---|---|
| 3,006,963 | 10/1961 | Buc et al. | 568/27 |
| 3,412,149 | 11/1968 | Schlör et al. | 564/85 |
| 3,907,899 | 9/1975 | Curran et al. | 568/23 |
| 3,923,794 | 12/1975 | Maruyama et al. | 568/56 |
| 4,141,916 | 2/1979 | Goralski | 260/556 |
| 4,476,321 | 10/1984 | Meyer et al. | 564/89 |
| 4,678,855 | 7/1987 | Shepard | 564/85 |
| 4,727,186 | 2/1988 | Schurter et al. | 564/85 |
| 4,734,527 | 3/1988 | Krauss | 568/23 |

FOREIGN PATENT DOCUMENTS 0044808 6/1982 European Pat. Off. .
0199871 10/1985 Japan .

OTHER PUBLICATIONS

Chem. Abstract 54 (1960) 7620I.
Chem. Abstract vol. 55 (1961) 17740a.
Adv. Org. Chem. 6, 356 (1969).
March, *Advanced Organic Chemistry*, etc. 2nd Ed. (1977) McGraw-Hill, New York, p. 374.
Durst, *Advanced Organic Chemistry*, etc. 6, (1969) 356.

*Primary Examiner*—Richard L. Raymond
*Assistant Examiner*—Peter G. O'Sullivan
*Attorney, Agent, or Firm*—Kevin T. Mansfield; Edward McC. Roberts

[57] ABSTRACT

A 2-(2-halogenoethylthio)-phenylsulfonamide of the formula I

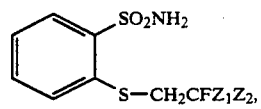
(I)

in which $Z_1$ and $Z_2$ independently of one another are hydrogen, fluorine or chlorine, is prepared by a process wherein:
a) a 2-halogenophenylsulfonamide of the formula II

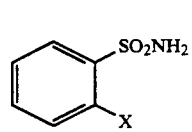
(II)

in which X is fluorine, chlorine or bromine, is converted, in the presence of a base, together with a mercaptan of the formula III

R-SH (III)

in which R is $C_1$–$C_6$alkyl or $C_1$–$C_6$alkyl substituted by phenyl, into a 2-sulfenylphenylsulfonamide,
b) this compound is oxidized to give the 2-sulfinylphenylsulfonamide,
c) the resulting 2-sulfinylphenylsulfonamide is converted, in the presence of an acid, into the disulfide of the formula VI

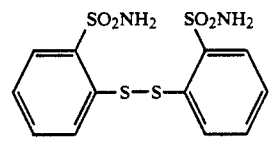
(VI)

d) the disulfide of the formula VI is reduced to the 2-mercaptophenylsulfonamide,
e) this compound is then converted, by means of a trialkylamine of the formula X $(R_1)_3N$ (X)

in which $R_1$ is $C_1$–$C_4$alkyl, into the 2-mercaptophenylsulfonamide trialkylamine salt, and
f) this compound is then reacted with a halogenofluoroethane of the formula IX $Y-CH_2CFZ_1Z_2$ (IX)

in which Y is chlorine or bromine and $Z_1$ and $Z_2$ independently of one another are hydrogen, fluorine or chlorine.

20 Claims, No Drawings

PROCESS FOR THE PREPARATION OF 2-(2-HALOGENOETHYLTHIO)-PHENYLSULFONAMIDES

The present invention relates to a process for the preparation of 2-(2-halogenoethylthio)-phenylsulfonamides of the formula I

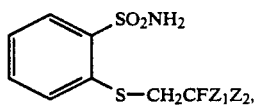  (I)

in which $Z_1$ and $Z_2$ independently of one another are hydrogen, fluorine or chlorine.

The 2-(2-halogenoethylthio)-phenylsulfonamides of the formula I are valuable intermediates for the preparation of herbicidally active N-phenylsulfonyl-N'-pyrimidinylureas and N-phenylsulfonyl-N'-triazinylureas such as are disclosed, for example, in European Patent Application No. 44,808.

Phenylsulfonylureas of this type derived from the 2-(2-halogenoethylthio)-phenylsulfonamides are distinguished by an advantageous degradation behaviour. There is, therefore, a need for an advantageous process for the preparation of the 2-(2-halogenoethylthio)-phenylsulfonamide of the formula I.

The object of the present invention is therefore to provide a process which makes it possible to prepare 2-(2-halogenoethylthio)-phenylsulfonamides in a simple manner and in good yields, starting from readily accessible starting materials.

It has now been found that the 2-(2-halogenoethylthio)-phenylsulfonamides of the formula I can be prepared in an advantageous manner if a) a 2-halogenophenylsulfonamide of the formula II

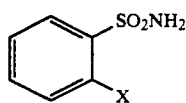  (II)

in which X is fluorine, chlorine or bromine, is converted, in the presence of a base, together with a mercaptan of the formula III

 R-SH  (III)

in which R is $C_1$–$C_6$alkyl or $C_1$–$C_6$alkyl substituted by phenyl, into a 2-sulfenylphenylsulfonamide of the formula IV

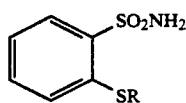  (IV)

in which R is as defined under formula III, b) this compound is oxidized to give the 2-sulfinylphenylsulfonamide of the formula V

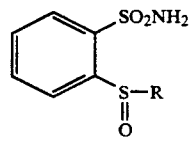  (V)

in which R is as defined under formula III, c) the resulting 2-sulfinylphenylsulfonamide of the formula V is converted, in the presence of an acid, into the disulfide of the formula VI

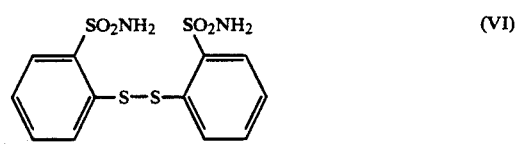  (VI)

d) the disulfide of the formula VI is reduced to the 2-mercaptophenylsulfonamide of the formula VII

  (VII)

e) this compound is then converted, by means of a trialkylamine of the formula X

 $(R_1)_3N$  (X)

in which $R_1$ is $C_1$–$C_4$alkyl, into the 2-mercaptophenylsulfonamide trialkylamine salt of the formula VIII

  (VIII)

in which $R_1$ is as defined under formula X, and f) this compound is then reacted with a halogenofluoroethane of the formula IX

 $Y$-$CH_2CFZ_1Z_2$  (IX)

in which Y is chlorine or bromine and $Z_1$ and $Z_2$ independently of one another are hydrogen, fluorine or chlorine.

The starting materials and the end products of the process according to the invention are known.

The compounds of the formulae III, IV, V, VII and IX are known and some are available commercially.

The disulfides of the formula VI and the 2-mercaptophenylsulfonamide trialkylamine salts of the formula VIII are novel and are also a subject of the present invention.

The $C_1$–$C_6$alkyl groups present in the substituent R can be linear or branched and are, for example, methyl, ethyl, n-propyl, isopropyl, n-butyl, sec-butyl, isobutyl, tert-butyl, n-pentyl or the isomeric pentyl radicals, n-hexyl or the isomeric hexyl radicals. The alkyl groups present in the substituent R preferably have 1 to 3 carbon atoms. If the alkyl groups are substituted by phenyl, they preferably have a chain length of 1 to 3 carbon atoms. It is particularly preferable for the substituent R to be benzyl.

The $C_1$-$C_4$alkyl groups present in the substituents $R_1$ can be linear or branched and are methyl, ethyl, n-propyl, isopropyl, n-butyl, sec-butyl or tert-butyl. It is particularly preferable for $R_1$ to be ethyl in each case.

The process stage a) of the process according to the invention is advantageously carried out in an inert solvent and at a temperature between +20° C. and boiling point of the solvent. The temperatures are usually between +20° and +180° C., preferably between +20° and +120° C. A particularly preferred temperature range is between +50° and +70° C.

Suitable solvents are chlorinated hydrocarbons, such as methylene dichloride, trichloromethane, trichloroethane, tetrachloroethane, chlorobenzene or dichlorobenzene; aromatic hydrocarbons, such as benzene, toluene or xylene; ethers, such as diethyl ether, diisopropyl ether, tetrahydrofuran or dioxane; nitriles, such as acetonitrile or propionitrile; cyclohexane, pyridine, N-methylpyrrolidone or N,N-dimethylformamide, N,N-dimethylformamide being particularly preferred.

The bases used are especially hydrides, hydroxides, carbonates or alcoholates of an alkali or alkaline earth metal, a trialkylamine or a pyridine base. Particularly preferred bases are pyridine, sodium hydroxide, sodium methylate, sodium ethylate, sodium carbonate or potassium carbonate. Potassium carbonate is very particularly preferred.

The process stage a) can be carried out in a particularly advantageous manner if 2-fluorophenylsulfonamide is employed as the 2-halogenophenylsulfonamide of the formula II.

Permanganates, periodates, per-acids or hydrogen peroxide are particularly suitable for use as oxidizing agents for process stage b).

Preferred oxidizing agents are peracetic acid, perbenzoic acid, periodic acid, potassium permanganate, potassium periodate and hydrogen peroxide. Hydrogen peroxide is a very particularly preferred oxidizing agent. The oxidation of the 2-sulfenylphenylsulfonamide of the formula IV is advantageously carried out at temperatures from 0° to +80° C., a temperature range from 0° to +40° C. being preferred.

In a preferred variant of the process according to the invention the oxidation of the 2-sulfenylphenylsulfonamide of the formula IV is carried out by means of hydrogen peroxide in the presence of acetic acid at a temperature from +5° to +15° C.

The process stage c) is preferably carried out at a temperature from +20° C. up to the boiling point of the solvent. Solvents which have proved particularly suitable are alcohols having a chain length of 1 to 4 carbon atoms, for example methanol, ethanol, propanol, isopropanol, butanol or 2-butanol. Methanol is a preferred solvent.

Acid-catalyst rearrangements of sulfoxides are known in the literature under the name "Pummerer rearrangements". Examples of reactions of this type are to be found in Adv. Org. Chem. 6,356 (1969). In contrast with the teaching known from this article, the acid-catalysed rearrangement of the 2-sulfinylphenylsulfonamide of the formula V does not lead to the 2-mercaptophenylsulfonamide, but leads, surprisingly and in a good yield and purity, to the 2,2'-bisaminosulfonyldiphenyl disulfide of the formula VI, which can be isolated from its reaction medium in a simple manner and has good stability on storage.

The reaction is not critical in respect of the nature of the acids used as catalysts. Preferred acids are mineral acids, in particular hydrochloric acid or sulfuric acid.

The process stages b) and c) can also be carried out immediately after one another in one reaction vessel, without the isolation of the intermediate of the formula V. The solvents suitable for this process variant are those mentioned in stage c).

The reductive cleavage of the disulfide of the formula VI to give the 2-mercaptophenylsulfonamide of the formula VII (process stage d)) is generally carried out at temperatures from +20° C. to +100° C.

The reduction is preferably carried out by means of hydrogen in the presence of noble metal catalysts or by means of zinc, iron or tin in the presence of hydrochloric acid or acetic acid or by means of sodium amalgam, magnesium amalgam or aluminium amalgam. Preferred reducing agents are hydrogen in the presence of platinum, palladium, rhodium or nickel catalysts, and also zinc, iron and tin in the presence of hydrochloric acid or acetic acid. Zinc in the presence of hydrochloric acid or acetic acid is a very particularly preferred reducing agent.

Both the purity and the stability on storage of the 2-mercaptophenylsulfonamide of the formula VII are considerably improved by the conversion of this intermediate into the corresponding trialkylamine salt of the formula VIII according to process stage e). Triethylamine is a trialkylamine of the formula X which is particularly suitable for the salt formation according to process stage e).

The reaction temperatures in the reaction of the 2-mercaptophenylsulfonamide trialkylamine salts with the halogenofluoroethane of the formula IX (process stage f) are between 0° and +80° C., preferably between 0° and +40° C. The reaction proceeds particularly advantageously if Y is bromine in formula IX. The solvents suitable for stage f) are those mentioned in stage a). It is advantageous to prepare compounds of the formula I in which $Z_1$ is hydrogen and $Z_2$ is hydrogen, fluorine or chlorine.

The process according to the invention is distinguished by numerous advantageous properties. Control of the reaction is not complicated (temperature, solvents, easy separation of intermediates and advantageous disposal of by-products and residues etc.). The process can be carried out with or without the isolation of the intermediate of the formula V. The disulfide of the formula VI and the trialkylamine salts of the formula VIII are particularly stable on storage. In addition, the process exhibits a high yield and a high product quality in each individual stage of the reaction.

The process according to the invention will be illustrated in greater detail by means of the following examples.

PREPARATION EXAMPLES

Example H1

Preparation of 2-benzylthiophenylsulfonamide

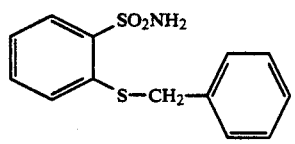

175.2 g of 2-fluorophenylsulfonamide and 160 g of potassium carbonate are added to a solution of 124.2 g of benzyl mercaptan in 400 ml of N,N-dimethylformamide. The reaction mixture is then heated at +60° C. for 3 hours. After the mixture has cooled to +25° C. it is filtered and the filtrate is then evaporated.

1500 ml of water are added to the residue obtained in this way, whereupon the product is precipitated in the form of colourless crystals. After the solution has been removed the resulting crystals are dissolved in ethyl acetate and then treated with magnesium sulfate. The mixture is filtered and the filtrate is evaporated to give 219 g (78.5% of theory) of 2-benzylthiophenylsulfonamide in the form of colourless crystals having a melting point of +104° to +106° C.

Example H2

Preparation of 2-benzylsulfinylphenylsulfonamide

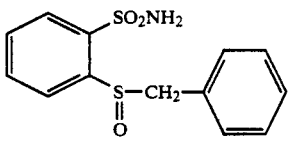

102 ml of 30% hydrogen peroxide solution are added dropwise at a temperature of +10° C. to a solution in 500 ml of concentrated acetic acid of 219 g of 2-benzylthiophenylsulfonamide obtained in accordance with Example H1. The reaction mixture is then stirred for 5 hours at a temperature of +25° C., in the course of which the product crystallizes out slowly. After the crystals have been separated off, washed with water and dried, 219 g (94.6%) of 2-benzylsulfinylphenylsulfonamide are obtained in the form of colourless crystals having a melting point of +206° to +209° C.

Example H3

Preparation of 2,2'-bisaminosulfonyldiphenyl disulfide

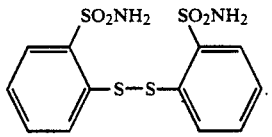 (VI)

500 ml of concentrated hydrochloric acid are added to a solution in 500 ml of methanol of 214 g of 2-benzylsulfinylphenylsulfonamide prepared in accordance with Example H2. After the reaction mixture has been boiled for 7 hours and kept at room temperature for 2 days, the precipitated disulfide is separated off and washed with water, isopropanol and diethyl ether. 133.2 g (97.7%) of theory of 2,2'-bisaminosulfonyldiphenyl disulfide are obtained in the form of yellowish crystals having a melting point of +217° C. (decomp.).

Example H4

Preparation of 2,2'-bisaminosulfonyldiphenyl disulfide

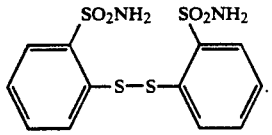 (VI)

50 ml of concentrated hydrochloric acid and 3.5 g of 30% hydrogen peroxide solution are added dropwise to a solution in 50 ml of ethanol of 10 g of 2-benzylthiophenylsulfonamide obtained in accordance with Example H1. The reaction mixture is then heated to reflux temperature for a period of 1 hour. After it has cooled to +25° C., the resulting crystals are separated off and washed with isopropanol and petroleum ether. 4 g of 2,2'-bisaminosulfonyldiphenyl disulfide are obtained in the form of yellow crystals having a melting point of +211° to +213° C.

Example H5

Preparation of 2-mercaptophenylsulfonamide

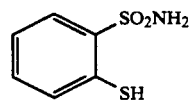 (VII)

18 g of zinc powder are added to a suspension in 180 ml of concentrated acetic acid of 23.2 g of 2,2'-bisaminosulfonyldiphenyl disulfide obtained in accordance with Example H3 and H4, and the mixture is heated at reflux temperature for 30 minutes. The suspension is then cooled to +17° C. and filtered. After the filter residue has been washed with ethyl acetate, the filtrate is evaporated and the residue is then dissolved in 200 ml of ethyl acetate. The solution is washed with twice 100 ml of water, dried with magnesium sulfate and evaporated. 22 g (94% of theory) of unpurified 2-mercaptophenylsulfonamide having a melting point of +113° to +140° C. are obtained.

Example H6

Preparation of 2-mercaptophenylsulfonamide triethylamine salt

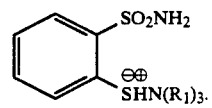 (VIII)

5 g of triethylamine are added dropwise, at a temperature of +25° C., to a solution in 60 ml of tetrahydrofuran of 7.6 g of 2-mercaptosulfonamide obtained in accordance with Example H5. The colourless crystals which have been precipitated are then separated off and washed with diethyl ether. 9.2 g of 2-mercaptophenylsulfonamide triethylamine salt having a melting point of +164° to +168° C. are obtained.

Example H7

Preparation of 2-(2-fluoroethylthio)-phenylsulfonamide

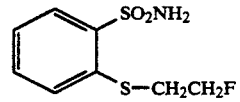

A mixture of 5.8 g of the 2-mercaptophenylsulfonamide triethylamine salt obtained in accordance with Example H6 and 1.7 g of 2-chloro-1-fluoroethane in 40 ml of methanol is stirred in a bomb tube for 23 hours at a temperature of +50° to +55° C. The reaction mixture is then evaporated and water is added to the residue which remains. The mixture is extracted with ethyl acetate, and the organic phase is washed and dried. Evaporation of the solution gives 3.5 g of 2-(2-fluoroethylthio)-phenylsulfonamide (74.5% of theory) having a melting point of +83° to +85° C.

Example H8

Preparation of 2-(2-fluoroethylthio)-phenylsulfonamide

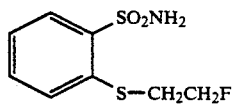

A mixture of 29 g of the 2-mercaptophenylsulfonamide triethylamine salt obtained in accordance with Example H6 and 2 g of 2-bromo-1-fluoroethane in 130 ml of tetrahydrofuran is stirred for 6 hours at a temperature of +40° C. to +45° C. The reaction mixture is then cooled to 0° C. and filtered. The filtrate is evaporated and the resulting residue is crystallized from methylene dichloride to give 21.2 g (90.2% of theory) of 2-(2-fluoroethylthio)-phenylsulfonamide having a melting point of +84° to +85° C.

Example H9

Preparation of 2-(2,2-difluoroethylthio)-phenylsulfonamide

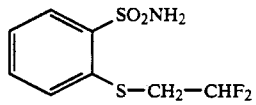

A mixture of 145.2 g of the 2-mercaptophenylsulfonamide triethylamine salt obtained in accordance with Example H6 and 79.7 g of 2-bromo-1,1-difluoroethane in 600 ml of methanol is stirred for 16 hours at a temperature of +55° C. to +60° C. The reaction mixture is then evaporated. Triturating the residue with ice water and filtering the suspension thus obtained gives 120 g (95% of theory) of 2-(2,2-difluoroethylthio)-phenylsulfonamide having a melting point of +111° C. to +112° C.

Example H10

Preparation of 2-(2-chloro-2-fluoroethylthio)-phenylsulfonamide

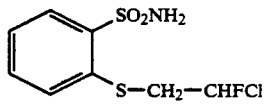

A mixture of 217.8 g of the 2-mercaptophenylsulfonamide triethylamine salt obtained in accordance with Example H6 and 101 g of 1,2-dichloro-1-fluoroethane in 950 ml of methanol is stirred for 24 hours at a temperature of +65° C. to +70° C. and is then stirred in an autoclave for a further 24 hours at +95° C. to +100° C. The reaction mixture is then evaporated and the residue is triturated with water. Extracting the mixture with ethyl acetate, washing the extract with water, drying it over sodium sulfate and evaporating it and purifying the residue by chromatography with methylene chloride gives 99.5 g (49.2% of theory) of 2-(2-chloro-2-fluoroethylthio)-phenylsulfonamide having a melting point of +88° C. to +89° C.

What is claimed is:

1. A process for the preparation of a 2-(2-halogenoethylthio)-phenylsulfonamide of the formula I

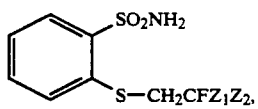

in which $Z_1$ and $Z_2$ independently of one another are hydrogen, fluorine or chlorine, which comprises a) reacting a 2-halogenophenylsulfonamide of the formula II

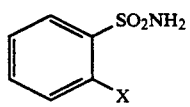

in which X is fluorine, chlorine or bromine, in the presence of a base and at a temperature from 20° to 180° C., with a mercaptan of the formula III $$R\text{-}SH \qquad (III)$$

in which R is $C_1$–$C_6$alkyl or $C_1$–$C_6$alkyl substituted by phenyl, to give a 2-sulfenylphenylsulfonamide of the formula IV

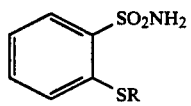

in which R is as defined under formula III, b) oxidizing a 2-sulfenylphenylsulfonamide of the formula IV with an oxidizing agent comprising hydrogen peroxide, peracetic acid, perbenzoic acid, periodic acid, potassium permanganate or potassium periodate at a temperature from 0° to 80° C. to give the 2-sulfinylphenylsulfonamide of the formula V

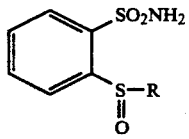

in which R is as defined under formula III, with or without isolation of the resulting 2-sulfinylphenylsulfonamide, converting the 2-sulfinylphenylsulfonamide of the formula V into the 2-mercaptophenylsulfonamide of the formula VII,

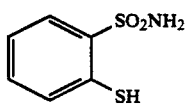

e) converting this compound by means of a trialkylamine of the formula X $(R_1)_3N$  (X)

in which $R_1$ is $C_1$–$C_4$alkyl, into the 2-mercaptophenylsulfonamide trialkylamine salt of the formula VIII

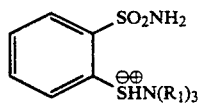  (VIII)

in which $R_1$ is as defined under formula X, and f) reacting the 2-mercaptophenylsulfonamide trialkylamine salt of the formula VIII at a temperature from 0° to 80° C. with a halogenofluoroethane of the formula IX $Y\text{-}CH_2CFZ_1Z_2$  (IX)

in which Y is chlorine or bromine and $Z_1$ and $Z_2$ independently of one another are hydrogen, fluorine or chlorine, the improvement in which process comprises c) converting the 2-sulfinylphenylsulfonamide of the formula V in the presence of an acid into the disulfide of the formula VI

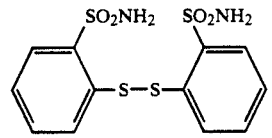  (VI)

and d) reducing the disulfide of the formula VI with a reducing agent comprising hydrogen in the presence of platinum, palladium, rhodium or nickel catalysts, or zinc, iron or tin in the presence of hydrochloric acid or acetic acid to the 2-mercaptophenylsulfonamide of the formula VII.

2. A process according to claim 1, wherein triethylamine is used as the trialkylamine of the formula X.

3. A process according to claim 1, wherein X is fluorine.

4. A process according to claim 1, wherein R is $C_1$–$C_3$alkyl or $C_1$–$C_3$alkyl which is substituted by phenyl.

5. A process according to claim 3, wherein R is $C_1$–$C_3$alkyl which is substituted by phenyl.

6. A process according to claim 4, wherein R is benzyl.

7. A process according to claim 1, wherein the base used in the reaction of the compound of the formula II with the compound of the formula III is a hydride, hydroxide, carbonate or alcoholate of an alkali or alkaline earth metal, a trialkylamine or a pyridine base.

8. A process according to claim 7, wherein the base used is pyridine, sodium hydroxide, sodium methylate, sodium ethylate, sodium carbonate or potassium carbonate.

9. A process according to claim 7, wherein the base used is potassium carbonate.

10. A process according to claim 1, wherein the oxidizing agent used is hydrogen peroxide.

11. A process according to claim 1, wherein the reducing agent used is zinc in the presence of hydrochloric acid or acetic acid.

12. A process according to claim 1, wherein the 2-sulfenylsulfonamide of the formula IV is converted directly into the disulfide of the formula VI without isolation of the intermediate of the formula V.

13. A process according to claim 1, wherein Y is bromine.

14. A process according to claim 1, wherein the reaction of the 2-halogenophenylsulfonamide of the formula II with the mercaptan of the formula III is carried out at a temperature from +20° to +120° C.

15. A process according to claim 1, wherein the oxidation of the 2-sulfenylphenylsulfonamide of the formula IV is carried out at a temperature from 0° to 40° C.

16. A process according to claim 1, wherein $Z_1$ is hydrogen and $Z_2$ is hydrogen, fluorine or chlorine.

17. A process according to claim 1, wherein a) a 2-fluorophenylsulfonamide of the formula II is converted, in the presence of a base and at a temperature from +50° to +70° C., by means of a benzyl mercaptan of the formula III into the 2-benzylthiophenylsulfonamide of the formula IV, b) this compound is oxidized by means of hydrogen peroxide at a temperature from +5° to +15° C. to give the 2-benzylsulfinylphenylsulfonamide of the formula V, c) this compound is converted in the presence of hydrochloric acid or sulfuric acid into the disulfide of the formula VI, d) the disulfide of the formula VI is reduced by means of zinc in the presence of acetic acid to give the 2-mercaptophenylsulfonamide of the formula VII, e) this compound is converted by means of triethylamine into the 2-mercaptophenylsulfonamide triethylamine salt of the formula VIII and f) this compound is then reacted with 2-bromo-1-fluoroethane, 2-bromo-1,1-difluoroethane, 2-bromo-1-chloro-1-fluoroethane or 1,2-dichloro-1-fluoroethane.

18. A process according to claim 17, wherein the base used is pyridine, sodium hydroxide, sodium methylate, sodium ethylate, sodium carbonate or potassium carbonate.

19. A process according to claim 18, wherein the base used is potassium carbonate.

20. A process according to claim 18, wherein the 2-benzylthiophenylsulfonamide of the formula IV is converted into the disulfide of the formula VI in the presence of hydrochloric acid and hydrogen peroxide without isolation of the intermediate of the formula V.

* * * * *